(12) United States Patent
Krishnan et al.

(10) Patent No.: US 7,949,167 B2
(45) Date of Patent: May 24, 2011

(54) AUTOMATIC LEARNING OF IMAGE FEATURES TO PREDICT DISEASE

(75) Inventors: Arun Krishnan, Exton, PA (US); Xiang Zhou, Exton, PA (US); Martin Huber, Uttenreuth (DE); Michael Kelm, Erlangen (DE); Joerg Freund, Munich (DE)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 237 days.

(21) Appl. No.: 12/427,974

(22) Filed: Apr. 22, 2009

(65) Prior Publication Data
US 2009/0310836 A1 Dec. 17, 2009

Related U.S. Application Data

(60) Provisional application No. 61/060,924, filed on Jun. 12, 2008, provisional application No. 61/076,787, filed on Jun. 30, 2008.

(51) Int. Cl.
*G06K 9/00* (2006.01)
*A61B 6/00* (2006.01)
*A61B 5/00* (2006.01)

(52) U.S. Cl. .............................. 382/128; 378/4; 600/300

(58) Field of Classification Search ............... 382/128, 382/129, 130, 131, 132, 133, 134, 164, 171, 382/173, 179; 378/4, 21–27, 137, 901; 600/300, 600/407, 410, 411, 425, 427, 431, 524; 128/920, 128/922
See application file for complete search history.

(56) References Cited

U.S. PATENT DOCUMENTS

| 5,768,413 A * | 6/1998 | Levin et al. ................. 382/173 |
| 7,428,323 B2 * | 9/2008 | Hillman ....................... 382/128 |

* cited by examiner

*Primary Examiner* — Abolfazl Tabatabai
(74) *Attorney, Agent, or Firm* — Peter Withstandley

(57) ABSTRACT

A method for training a computer system for automatic detection of regions of interest includes receiving patient records. For each of the received patient records a text field and a medical image are identified from within the patient record and the medical image is automatically segmented to identify a structure of interest. The text field is searched for one or more keywords indicative of a particular abnormality associated with the structure of interest. The medical image is added to a grouping representing the particular abnormality when the text field indicates that the patient has the particular abnormality and the medical image is added to a grouping representing the absence of the particular abnormality when the text field does not indicate that the patient has the particular abnormality. The groupings of medical images are used to automatically train a computer system for the subsequent detection of the particular abnormality.

20 Claims, 3 Drawing Sheets

AUTOMATIC LEARNING OF IMAGE FEATURES TO PREDICT DISEASE

CROSS-REFERENCE TO RELATED APPLICATION

The present application is based on U.S. Provisional Application Ser. No. 61/060,924, filed Jun. 12, 2008 and U.S. Provisional Application Ser. No. 61/076,787, filed Jun. 30, 2008, the entire contents of which are herein incorporated by reference.

BACKGROUND OF THE INVENTION

1. Technical Field

The present disclosure relates to disease prediction and, more specifically, to automatic learning of image features to predict disease.

2. Discussion of Related Art

Computer aided diagnosis (CAD) pertains to the use of artificial intelligence to process medical image data and locate one or more regions of interest within the medical image data. These regions of interest may correspond to, for example, locations that are determined to be of an elevated likelihood for including an anatomical irregularity that may be associated with a disease, injury or defect. Often CAD is used to identify regions that appear to resemble lesions.

In general, CAD may be used to identify regions of interest that may then be inspected closely by a trained medical professional such as a radiologist. By utilizing CAD, a radiologist can reduce the chances of failing to properly identify a lesion and may be able to examine a greater number of medical images in less time and with improved accuracy.

There are many varying approaches for performing CAD. Some of these approaches utilize complex algorithms for detecting suspicious regions from normal regions. These algorithms may be manually programmed at great time and expense. However, other approaches rely on computer learning. In computer learning, a learning algorithm is provided with a set of training data that includes images in which a trained medical professional, such as a radiologist, has diagnosed a particular disease as well as images in which a radiologist has determined that the subject is free of the particular disease. By analyzing the set of images that are known to show the particular disease and the set of images that are known to not show the particular disease, the learning algorithm can determine how to differentiate between subsequent images that may or may not have the particular disease.

Moreover, such computer learning techniques may be used to differentiate between regions of a medical image that may be suspected of having a particular disease and regions of a medical image that may be free of the particular disease so that precise regions of suspicion may be identified within the medical image. The radiologist may then treat each detected region of suspicion as a lesion candidate and may render a final diagnosis based on the CAD results.

One way in which learning algorithms use training data to help identify regions of suspicion in subsequent medical images is to develop a set of image features that can predict the particular disease. Accordingly, learning algorithms may determine which image features are both highly represented in instances of actual lesions and yet poorly represented in the absence of lesions. Given sufficient training data, numerous useful image features may be developed.

In training these learning algorithms, it is beneficial to provide a large set of training data. Insufficient training data may result in ineffective search or detection algorithms, for example, insufficient and/or ineffective image features. However, obtaining sufficient training data can be a time consuming and expensive endeavor and may divert resources away from other important areas of development. This is because in order to provide training data, studies must be performed and/or clinical data must be manually reviewed for each particular disease that one wishes to be able to train the CAD system to detect. For example, if it is desired that the CAD system be trained to find lung nodule candidates, clinical data must be reviewed to find medical images with confirmed instances of lung nodules and to find other medical images with confirmed absence of instances of lung nodules. These images may then be provided to the learning algorithm as training data. As a large amount of training data must be collected to accurately train the CAD system, the training process can be very demanding. Moreover, where it is desired that the CAD system be able to detect multiple different forms of illness, the amount of training data to be identified and sorted can become enormous.

SUMMARY

A method for training a computer system for automatic detection of regions of interest in medical image data using a computer-based image processing device includes receiving a plurality of patient records from an electronic medical records database. For each of the received patient records a text field and a medical image are identified from within the patient record. The medical image is automatically segmented to identify a structure of interest. The text field is searched for one or more keywords indicative of a particular abnormality associated with the structure of interest. It is determined whether the text field indicates that the patient has the particular abnormality. The medical image is added to a grouping of medical images representing the particular abnormality when it is determined that the text field indicates that the patient has the particular abnormality and the medical image is added to a grouping of medical images representing the absence of the particular abnormality when it is determined that the text field does not indicate that the patient has the particular abnormality. The grouping of medical images representing the particular abnormality and the grouping of medical images representing the absence of the particular abnormality are used to automatically train a computer system for the subsequent detection of the particular abnormality.

For each of the records, the medical image may be a CT scan, an MRI, a PET or SPECT scan, photograph or an ultrasound image. For each of the records, the text field may be a radiology report corresponding to the medical image.

The structure of interest may be a particular organ. The particular abnormality may be a particular disease, injury or defect of the particular organ. Alternatively, or additionally, the particular abnormality could span multiple organs.

Determining whether the text field indicates that the patient has the particular abnormality may include searching the text field for keywords that are indicative of a positive diagnosis for the particular abnormality.

Training the computer system for the subsequent detection of the particular abnormality may include developing one or more classifiers based on the grouping of medical images representing the particular abnormality and the grouping of medical images representing the absence of the particular abnormality.

Using the grouping of medical images representing the particular abnormality and the grouping of medical images representing the absence of the particular abnormality to automatically train for the subsequent detection of the particular abnormality may include using the grouping of medical images representing the particular abnormality and the grouping of medical images representing the absence of the particular abnormality as training data for a computer-learning operation.

A method for automatic detection of regions of interest in medical image data using a computer-based image processing device includes receiving a plurality of patient records from an electronic medical records database, and for each of the received patient records: identifying a text field and a medical image from within the patient record, automatically segmenting the medical image to identify a structure of interest, searching the text field for one or more keywords indicative of a particular abnormality associated with the structure of interest, determining whether the text field indicates that the patient has the particular abnormality, and adding the medical image to a grouping of medical images representing the particular abnormality when it is determined that the text field indicates that the patient has the particular abnormality and adding the medical image to a grouping of medical images representing the absence of the particular abnormality when it is determined that the text field does not indicate that the patient has the particular abnormality. The grouping of medical images representing the particular abnormality and the grouping of medical images representing the absence of the particular abnormality are used to automatically train a computer-learning algorithm. A subsequent medical image of a subsequent patient is acquired. The trained computer-learning is used to analyze the subsequent medical image to aid in determining whether the subsequent patient has the particular abnormality.

For each of the records, the medical image may be a CT scan, an MRI, a PET or SPECT scan, photograph or an ultrasound image. For each of the records, the text field may be a radiology report corresponding to the medical image.

The structure of interest may be a particular organ. The particular abnormality may be a particular disease, injury or defect of the particular organ. Determining whether the text field indicates that the patient has the particular abnormality may include searching the text field for keywords that are indicative of a positive diagnosis for the particular abnormality.

Training the computer-learning algorithm may include developing one or more classifiers based on the grouping of medical images representing the particular abnormality and the grouping of medical images representing the absence of the particular abnormality.

A computer system includes a processor and a program storage device readable by the computer system, embodying a program of instructions executable by the processor to perform method steps for training a computer system for automatic detection of regions of interest. The method includes receiving a plurality of patient records from an electronic medical records database, and for each of the received patient records, identifying a text field and a medical image from within the patient record, automatically segmenting the medical image to identify a structure of interest, determining whether the text field indicates that the patient has a particular abnormality associated with the structure of interest, and adding the medical image to a grouping of medical images representing the particular abnormality when it is determined that the text field indicates that the patient has the particular abnormality and adding the medical image to a grouping of medical images representing the absence of the particular abnormality when it is determined that the text field does not indicate that the patient has the particular abnormality. The grouping of medical images representing the particular abnormality and the grouping of medical images representing the absence of the particular abnormality are used to automatically train a computer system for the subsequent detection of the particular abnormality.

For each record, the text field may be a radiology report corresponding to the medical image. The report could be, for example a transcribed version of a dictated report. In another example, the report could be a scanned and OCR (optical character recognized) version of a written report. The text field could also be any other form of text that either originated as digital text or was digitized by some text recognition means. The structure of interest may be a particular organ and the particular abnormality is a particular disease, injury or defect of the particular organ.

Determining whether the text field indicates that the patient has the particular abnormality may include searching the text field for keywords that are indicative of a positive diagnosis for the particular abnormality.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
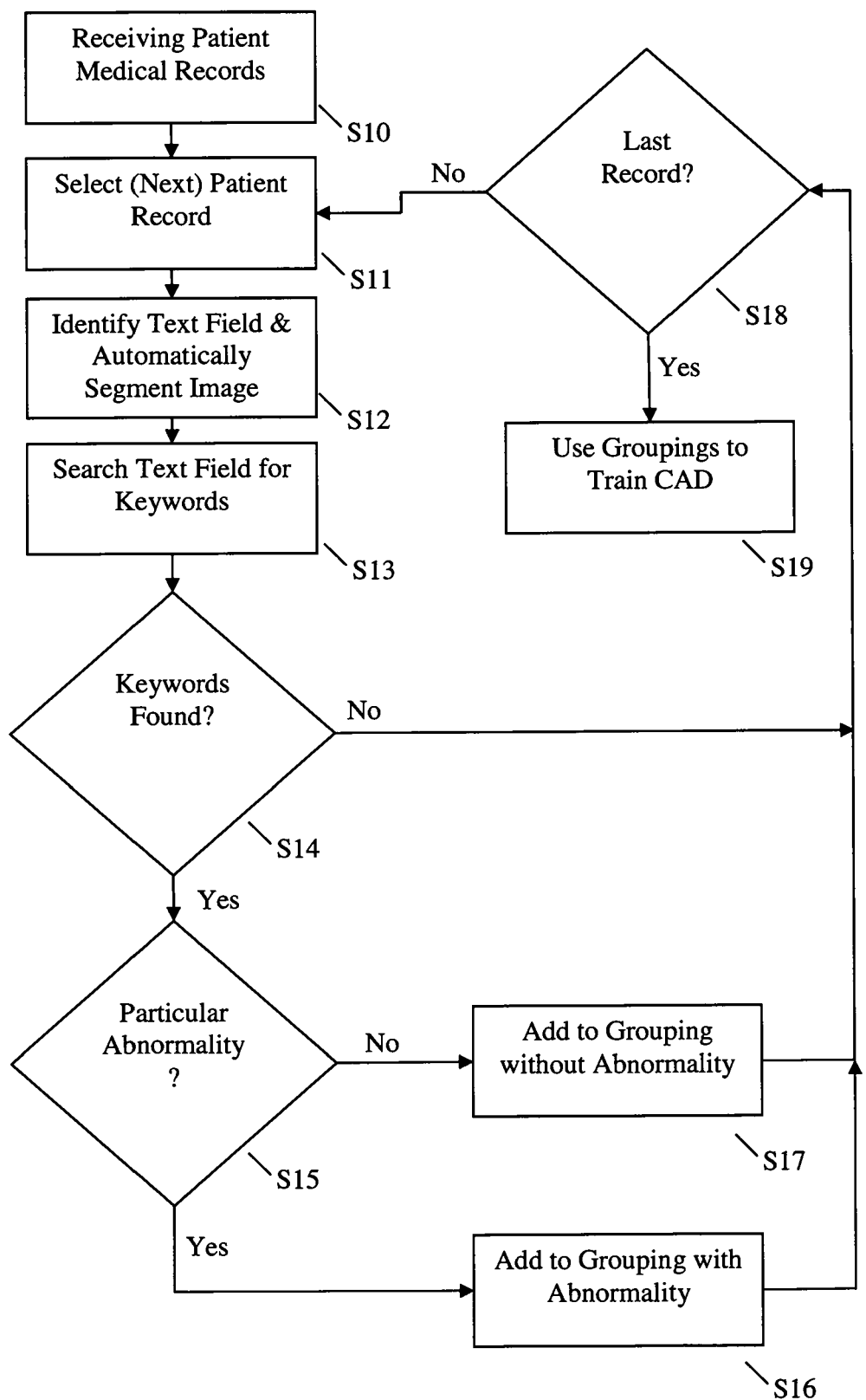
FIG. 1 is a flow chart illustrating a method for automatically detecting regions of interest in, and the abnormality-based grouping of, medical images according to exemplary embodiments of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide an approach for automatic learning of image features to predict disease in which training data may be automatically parsed from electronic patient records databases. Accordingly, rather than having to rely on training data that has been specifically generated based on expert markings to show the location of nodules and lesions, exemplary embodiments of the present invention may automatically generate a very large set of training data from existing patient records.

Exemplary embodiments of the present invention may begin with text mining in which radiology reports may be automatically parsed and grouped based on various disease concepts. Images that correspond to the reports may then be used to automatically learn ways of distinguishing between subsequent images with and without the particular disease. Thus, the image groups may be recreated based on image features that are automatically generated.

Figure 2:
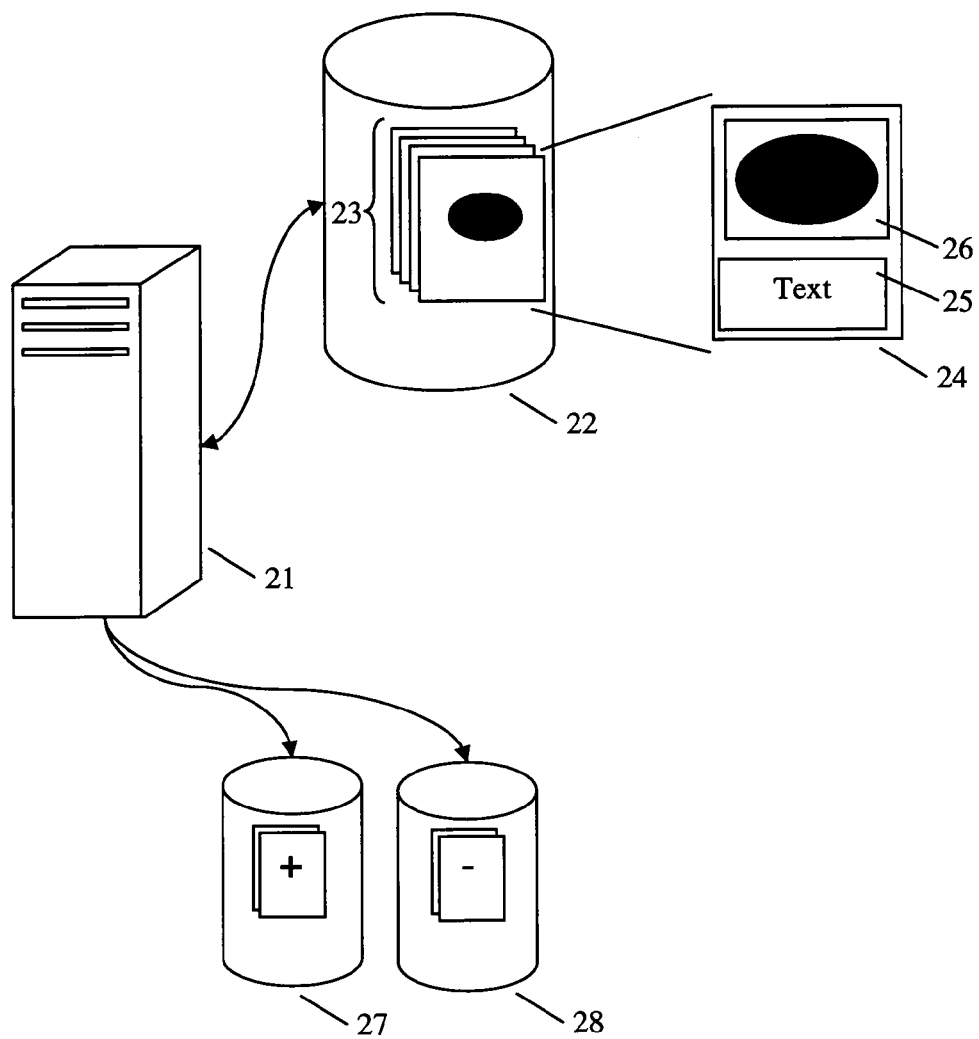
FIG. 2 is a block diagram illustrating a system for automatically detecting regions of interest in, and the abnormality-based grouping of, medical images according to exemplary embodiments of the present invention.

FIG. 1 is a flow chart illustrating a method for automatically detecting regions of interest in medical images according to exemplary embodiments of the present invention. FIG. 2 is a block diagram illustrating a system for automatically detecting regions of interest in medical images according to exemplary embodiments of the present invention.

Referring to FIGS. 1 and 2, first patient medical records may be accessed (Step S10). The patient medical records may be accessed by a computer system 21, for example, from a database of patient medical records 22. The database of medical records 22 may be an electronic medical records (EMR) system, also known as an electronic health records (EHR) system, or a personal health records (PHR) system. The database 22 may also include multiple distinct records databases and thus exemplary embodiments of the present invention may be utilized to pull patient records across a large number of records databases from diverse sources.

The database 22 may include a set 23 of individual patient records 234. Each individual patient record 24 may include a radiologists report or similar medical interpretation of medical image data. The radiologist report may include an actual medical image 26 along with one or more text fields 25 that include the interpretation of the medical image data.

Thus after the patient records have been accessed (Step S10) by the computer system 21, a patient record may be selected (Step S11). The patient record may be selected either at random or systematically from the available records of the database 22. When it is desired that only a subset of the patient records be used, an individual patient record may be selected in accordance with pre-determined eligibility parameters and/or at random. Where it is desired that every available record be used, each record may be systematically called up by the computer system.

Then a text field 25 within a radiologist's report may be automatically identified from within the selected patient record and the medical image may be automatically segmented to identify a relevant anatomical structure and/or organ (Step S12). The text field 25 may be identified, for example, in accordance with field tags and/or word identification.

As each disease may be associated with a particular organ or other anatomical structure, exemplary embodiments of the present invention may be able to automatically segment a plurality of organs and/or anatomical structures from the medical image data to identify a particular organ or structure that is associated with the particular disease the CAD system is being trained to detect. Automatic segmentation may be performed, for example, using an automatic segmentation system such as ALPHA developed by Siemens Corporation. Alternatively, other approaches for automatic segmentation may be used.

The text field 25 may then be searched for one or more keywords and/or key-phrases that may be indicative of a particular abnormality (Step S13). The keywords and/or key-phrases may be called up from a keyword database. The keywords and/or key-phrases may be predetermined and may include multiple names for a particular abnormality, various identifying symptoms and/or medical billing codes as well as various words that are indicative of the absence of the particular disease or other diagnosis that may appear similar to the particular disease.

A keyword match may be achieved when either one keyword and/or key-phrase is found or a particular number of points may be assigned to each of the various keywords and key-phrases and a match may be achieved when a threshold number of points are matched. Other approached may be followed for ascertaining a match. Regardless of the approach being used, where a keyword match is not achieved (No, S14), then a next patient record may be selected (Step S11) as long as the selected record was not the last record (No, Step S18).

If a keyword match is achieved (Yes, Step S14), then it may be determined whether the particular abnormality is positive or negative (Step S15). This step may include automatically interpreting the text field 25 data to determine if the present language is indicative of a positive finding of the particular abnormality or a negative finding of the particular abnormality. This step may also include a reach for keywords and/or key-terms as well as an assignment of points. For example, certain words and phrases may be assigned a positive number of points to the extent that they indicate a positive diagnosis and other words and phrases may be assigned a negative number of points to the extent that they indicate a negative diagnosis. An average may then be calculated based on all of the various matches and a positive point average over a particular threshold may indicate that the particular abnormality is present while a negative average over a particular threshold may indicate that the particular abnormality is not present. Where the threshold is not met, it may not be certain whether the diagnosis is positive or negative and the selected patient record may be excluded from consideration.

If, however, it is determined that the patient record indicates a positive presence of the particular abnormality (Yes, Step S15) then the image data 26 associated with the particular text field 25 may be added to a grouping of positive cases of the abnormality 27 (Step S16). If, on the other hand, it is determined that the patient record indicates the absence of the particular abnormality (No, Step S15) then the image data 26 associated with the particular text field 25 may be added to a grouping of cases without the abnormality 28 (Step S17). In either event, and in the event that no determination can be made as to whether the particular abnormality is present, the next patient record may be selected (Step S11) as long as the present patient record is not the last record (No, Step S18).

When the present patient record is in fact the last patient record (Yes, Step S18) then the positive and negative grouping 27 and 28 may be used as training data to train the learning CAD algorithms (Step S19). In this step, it is not necessary to use the entire medical image data as the training data, rather, it may be sufficient to use only the automatically segmented organ or anatomical structure that pertains to the particular disease.

Learning may be performed, for example, by providing the images of the positive grouping 27 and the images of the negative grouping 28 to a learning algorithm as training data. However, the learning algorithm need not consider the entire medical images as training data. Rather, the learning algorithm may utilize only an organ or other bodily structure that is pertinent to the particular disease. For example, if the particular disease is lung nodules, then the lungs may be segmented from the medical image data and thus the positive training data may simply include segmented lungs including a lung nodule and the negative training data may simply include segmented lungs that are free of lung nodules.

Exemplary embodiments of the present invention may parse patient records for multiple diseases, for example, at the same time, so that the patient medical records need only be accessed once to train a CAD system for a plurality of detections. Thus there may be multiple diseases being searched for. Each disease may be associated with a particular organ or other anatomical structure, and thus, exemplary embodiments of the present invention may be able to automatically segment a plurality of organs and anatomical structures from the medical image data. Automatic segmentation may be performed, for example, using an automatic segmentation system such as ALPHA developed by Siemens Corporation. Alternatively, other approaches for automatic segmentation may be used.

Figure 3:
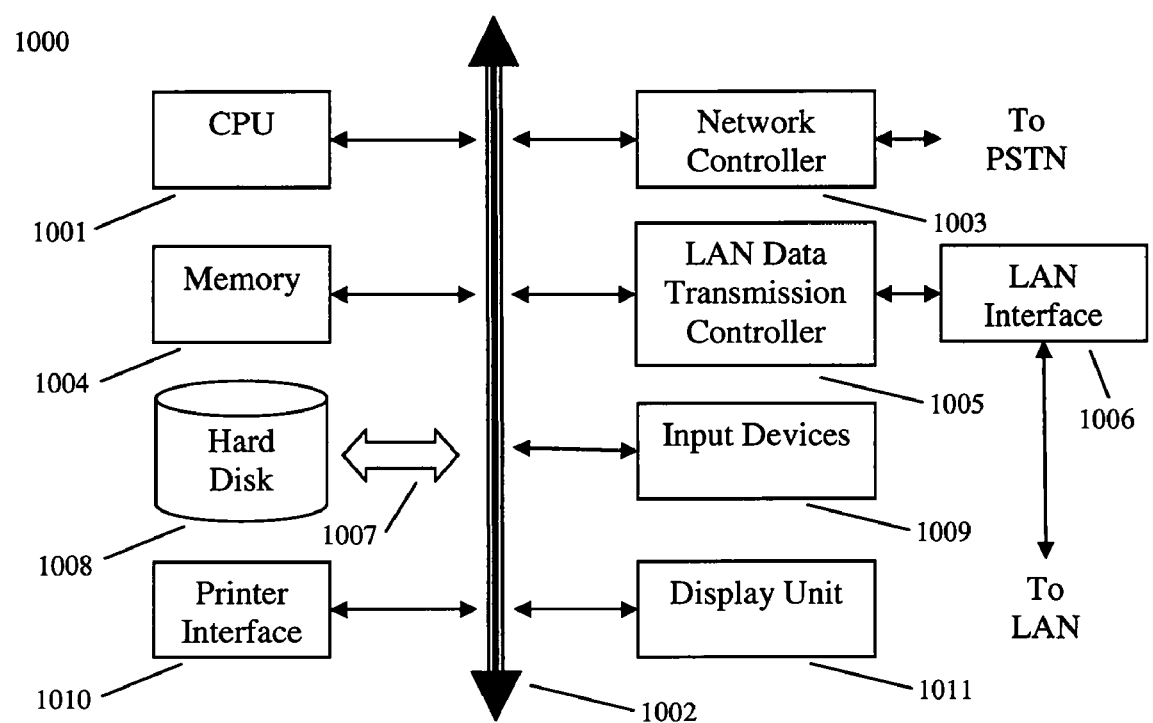
FIG. 3 shows an example of a computer system capable of implementing the method and apparatus according to embodiments of the present disclosure.

FIG. 3 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for training a computer system for automatic detection of regions of interest in medical image data using a computer-based image processing device, comprising:
   receiving a plurality of patient records from an electronic medical records database, and for each of the received patient records:
      identifying a text field and a medical image from within the patient record;
      automatically segmenting the medical image to identify a structure of interest;
      searching the text field for one or more keywords indicative of a particular abnormality associated with the structure of interest;
      determining whether the text field indicates that the patient has the particular abnormality; and
      adding the medical image to a grouping of medical images representing the particular abnormality when it is determined that the text field indicates that the patient has the particular abnormality and adding the medical image to a grouping of medical images representing the absence of the particular abnormality when it is determined that the text field does not indicate that the patient has the particular abnormality, and
   using the grouping of medical images representing the particular abnormality and the grouping of medical images representing the absence of the particular abnormality to automatically train a computer system for the subsequent detection of the particular abnormality.

2. The method of claim 1, wherein for all records, the medical image is a CT scan, an MRI, a PET or SPECT scan, photograph or an ultrasound image.

3. The method of claim 1, wherein for each record, the text field is from a radiology report corresponding to the medical image.

4. The method of claim 1, wherein the structure of interest is a particular organ.

5. The method of claim 4, wherein the particular abnormality is a particular disease, injury or defect of the particular organ.

6. The method of claim 1, wherein determining whether the text field indicates that the patient has the particular abnormality includes searching the text field for keywords that are indicative of a positive diagnosis for the particular abnormality.

7. The method of claim 1, wherein training the computer system for the subsequent detection of the particular abnormality includes training one or more classifiers based on the grouping of medical images representing the particular abnormality and the grouping of medical images representing the absence of the particular abnormality.

8. The method of claim 1, wherein using the grouping of medical images representing the particular abnormality and the grouping of medical images representing the absence of the particular abnormality to automatically train for the subsequent detection of the particular abnormality includes using the grouping of medical images representing the particular abnormality and the grouping of medical images representing the absence of the particular abnormality as training data for a machine-learning operation.

9. A method for automatic detection of regions of interest in medical image data using a computer-based image processing device, comprising:
   receiving a plurality of patient records from an electronic medical records database, and for each of the received patient records:
      identifying a text field and a medical image from within the patient record;
      automatically segmenting the medical image to identify a structure of interest;
      searching the text field for one or more keywords indicative of a particular abnormality associated with the structure of interest;
      determining whether the text field indicates that the patient has the particular abnormality; and
      adding the medical image to a grouping of medical images representing the particular abnormality when it is determined that the text field indicates that the patient has the particular abnormality and adding the medical image to a grouping of medical images representing the absence of the particular abnormality when it is determined that the text field does not indicate that the patient has the particular abnormality, and
   using the grouping of medical images representing the particular abnormality and the grouping of medical images representing the absence of the particular abnormality to automatically train a computer-learning algorithm;
   acquiring a subsequent medical image of a subsequent patient; and
   using the trained computer-learning algorithm to analyze the subsequent medical image to aid in determining whether the subsequent patient has the particular abnormality.

10. The method of claim 9, wherein for all records, the medical image is a CT scan, an MRI, a PET or SPECT scan, photograph or an ultrasound image; and the subsequent medical image is of the same modality as the records.

11. The method of claim 9, wherein for each record, the text field is from a radiology report corresponding to the medical image.

12. The method of claim 9, wherein the structure of interest is a particular organ.

13. The method of claim 9, wherein the particular abnormality is a particular disease, injury or defect of the particular organ.

14. The method of claim 9, wherein determining whether the text field indicates that the patient has the particular abnormality includes searching the text field for keywords that are indicative of a positive diagnosis for the particular abnormality.

15. The method of claim 9, wherein training the computer-learning algorithm includes developing one or more classifiers based on the grouping of medical images representing the particular abnormality and the grouping of medical images representing the absence of the particular abnormality.

16. A computer system comprising:
 a processor; and
 a program storage device readable by the computer system, embodying a program of instructions executable by the processor to perform method steps for training a computer system for automatic detection of regions of interest, the method comprising:
 receiving a plurality of patient records from an electronic medical records database, and for each of the received patient records:
  identifying a text field and a medical image from within the patient record;
  automatically segmenting the medical image to identify a structure of interest;
  determining whether the text field indicates that the patient has a particular abnormality associated with the structure of interest; and
  adding the medical image to a grouping of medical images representing the particular abnormality when it is determined that the text field indicates that the patient has the particular abnormality and adding the medical image to a grouping of medical images representing the absence of the particular abnormality when it is determined that the text field does not indicate that the patient has the particular abnormality, and
 using the grouping of medical images representing the particular abnormality and the grouping of medical images representing the absence of the particular abnormality to automatically train a computer system for the subsequent detection of the particular abnormality.

17. The computer system of claim 16, wherein for each record, the text field is from a radiology report corresponding to the medical image.

18. The computer system of claim 16, wherein the structure of interest is a particular organ and the particular abnormality is a particular disease, injury or defect of the particular organ.

19. The computer system of claim 16, wherein determining whether the text field indicates that the patient has the particular abnormality includes searching the text field for keywords that are indicative of a positive diagnosis for the particular abnormality.

20. The computer system of claim 16, wherein training the computer system for the subsequent detection of the particular abnormality includes developing one or more classifiers based on the grouping of medical images representing the particular abnormality and the grouping of medical images representing the absence of the particular abnormality.

\* \* \* \* \*